United States Patent
Lindsay et al.

(10) Patent No.: US 10,137,030 B2
(45) Date of Patent: Nov. 27, 2018

(54) SELF-TITRATABLE MANDIBULAR REPOSITIONING DEVICE

(71) Applicant: Sleep Science Partners, Inc., Larkspur, CA (US)

(72) Inventors: Noel Lindsay, Ross, CA (US); Glenn Clark, Culver City, CA (US); Heather Flick, Belvedere, CA (US)

(73) Assignee: Sleep Science Partners, Inc., Larkspur, CA (US)

( * ) Notice: Subject to any disclaimer, the term of this patent is extended or adjusted under 35 U.S.C. 154(b) by 1173 days.

(21) Appl. No.: 14/158,850

(22) Filed: Jan. 19, 2014

(65) Prior Publication Data

US 2014/0130809 A1    May 15, 2014

Related U.S. Application Data

(63) Continuation of application No. 12/826,553, filed on Jun. 29, 2010, now Pat. No. 9,631,800.

(60) Provisional application No. 61/221,515, filed on Jun. 29, 2009.

(51) Int. Cl.
   *A61F 5/56*    (2006.01)
(52) U.S. Cl.
   CPC .................................. *A61F 5/566* (2013.01)
(58) Field of Classification Search
   CPC .. A61F 5/566; A61C 5/90; A61C 7/08; A63B 71/085
   USPC ........... 433/41–42, 44–45, 19; 128/848, 859, 128/861–862
   See application file for complete search history.

(56) References Cited

U.S. PATENT DOCUMENTS

| | | | |
|---|---|---|---|
| 5,313,960 A | 5/1994 | Tomasi | |
| 5,499,633 A | 3/1996 | Fenton | |
| 5,823,193 A | 10/1998 | Singer et al. | |
| 5,868,138 A * | 2/1999 | Halstrom | A61F 5/566 128/848 |
| 6,170,485 B1 | 1/2001 | Orrico | |
| 7,520,281 B1 * | 4/2009 | Nahabedian | A61F 5/566 128/848 |
| 8,631,800 B2 | 1/2014 | Lindsay et al. | |
| 2006/0105287 A1 * | 5/2006 | Wilburn | A61C 7/08 433/24 |
| 2011/0017220 A1 | 1/2011 | Lindsay | |

* cited by examiner

*Primary Examiner* — Kari Rodriquez
(74) *Attorney, Agent, or Firm* — Carr & Ferrell LLP

(57) ABSTRACT

The present technology provides a mandibular repositioning device (MRD) which may be self titratable. The MRD may be repositioned relative to the maxilla, e.g., the mandible may be brought, via the device, to a position forward of a neutral resting and/or bite position. The MRD allows for adjusting the maintained forward position by simply biting-down to preserve the desired degree of mandibular advancement. The present technology also allows for movement of the mandible in a lateral direction. The lateral movement is allowed for any forward longitudinal positioning of the mandible. The MRD may use a plurality of components that are coupled together and allow for lateral and longitudinal motion between each other. The present technology may be used in MRDs which may be self-fitted, typically by immersing the device in hot water and then biting into the device, making an impression of the teeth in the softened thermoplastic polymer. It may also be applied to MRDs that do not require any fitting to the teeth and to devices that are custom-fabricated by dental labs.

2 Claims, 5 Drawing Sheets

SELF-TITRATABLE MANDIBULAR REPOSITIONING DEVICE

CROSS-REFERENCE TO RELATED APPLICATION

The present continuation application claims the benefit and priority of U.S. non-provisional patent application Ser. No. 12/826,553, filed on Jun. 29, 2010, now U.S. Pat. No. 8,631,800, issued on Jan. 21, 2014 and titled "Self-Titratable Mandibular Repositioning Device," which in turn claims the priority benefit of U.S. provisional patent application No. 61/221,515, filed Jun. 29, 2009 and entitled "Titratable Self-Fitted Mandibular Repositioning Device." All of the aforementioned disclosures are hereby incorporated by reference herein in thier entireties including all references cited therein.

BACKGROUND OF THE INVENTION

A mandibular repositioning device (MRD) operates to position a mandible of a user in such a way as to help prevent snoring and sleep apnea in the user. Typically, the MRD works to position the mandible, the lower jaw bone, in a position that is forward from a neutral mandible position. As a result, the MRD helps eliminate snoring and sleep apnea.

Many MRDs allow the amount of mandibular advancement to be adjusted or titrated. However, most titration mechanisms have disadvantages. For example, one such mechanism utilizes elastic bands to apply pressure to keep the lower component of the MRD in a forward position. Such devices may provide different degrees of mandibular advancement through the selection of elastic bands from a variety of such bands of various different lengths. Therefore the ability to titrate such a device is limited by the variety of available elastic bands and the fitting process may require the user to try a number of different sets of elastic bands before finding one that most closely matches the desired degree of mandibular advancement. These bands also wear out and must be replaced periodically.

Another titration mechanism keeps the mandible in a forward position by use of a bracket. The bracket keeps the mandible in the forward position more consistently than an elastic band MRD, but is more expensive to manufacture. While devices utilizing this kind of mechanism allow any degree of mandibular advancement, the titration process may also require a trial-and-error process that may be quite time-consuming.

What is needed is an efficient, reliable MRD that holds a forward position of a mandible and is more easily adjustable by the user.

SUMMARY OF THE INVENTION

The present technology provides a mandibular repositioning device (MRD) which may be self titratable and self fitted. The mandible may be repositioned relative to the maxilla, e.g., the mandible may be brought, via the device, to a position forward of a neutral resting and/or bite position. The MRD allows for adjusting the maintained forward position and allows for movement of the mandible in a lateral direction. One useful and unique element of the present technology is that the MRD allows the user to advance his or her jaw by any amount and, when it's comfortable, allows the user to lock-in that amount of mandibular advancement by simply biting down on the MRD. The lateral movement is allowed for any forward longitudinal positioning of the mandible. The MRD may use a plurality of components that are coupled together and allow for lateral and longitudinal motion between each other.

A MRD may include a lower component and an upper component. The lower component may be configured to engage a mandible of a user and may include a clip. The upper component may be configured to engage a maxilla of the user and include a first groove. The first groove may be configured to receive the clip and thereby couple the lower component to the upper component. The lower component and the upper component may be maintained in a fixed position by the clip and the first groove.

A mandibular repositioning device may include a plurality of components, a first mechanism and a second mechanism. The first component may receive a user's top teeth and a second component may receive a user's bottom teeth. The first mechanism may couple together at least two of the plurality of components and allow movement of the user's mandible in a longitudinal direction while the MRD is positioned within the user's mouth. The second mechanism may couple together at least two of the plurality of components and allow movement of the user's mandible in a lateral direction while the MRD is positioned within the user's mouth.

DETAILED DESCRIPTION

Figure 1:
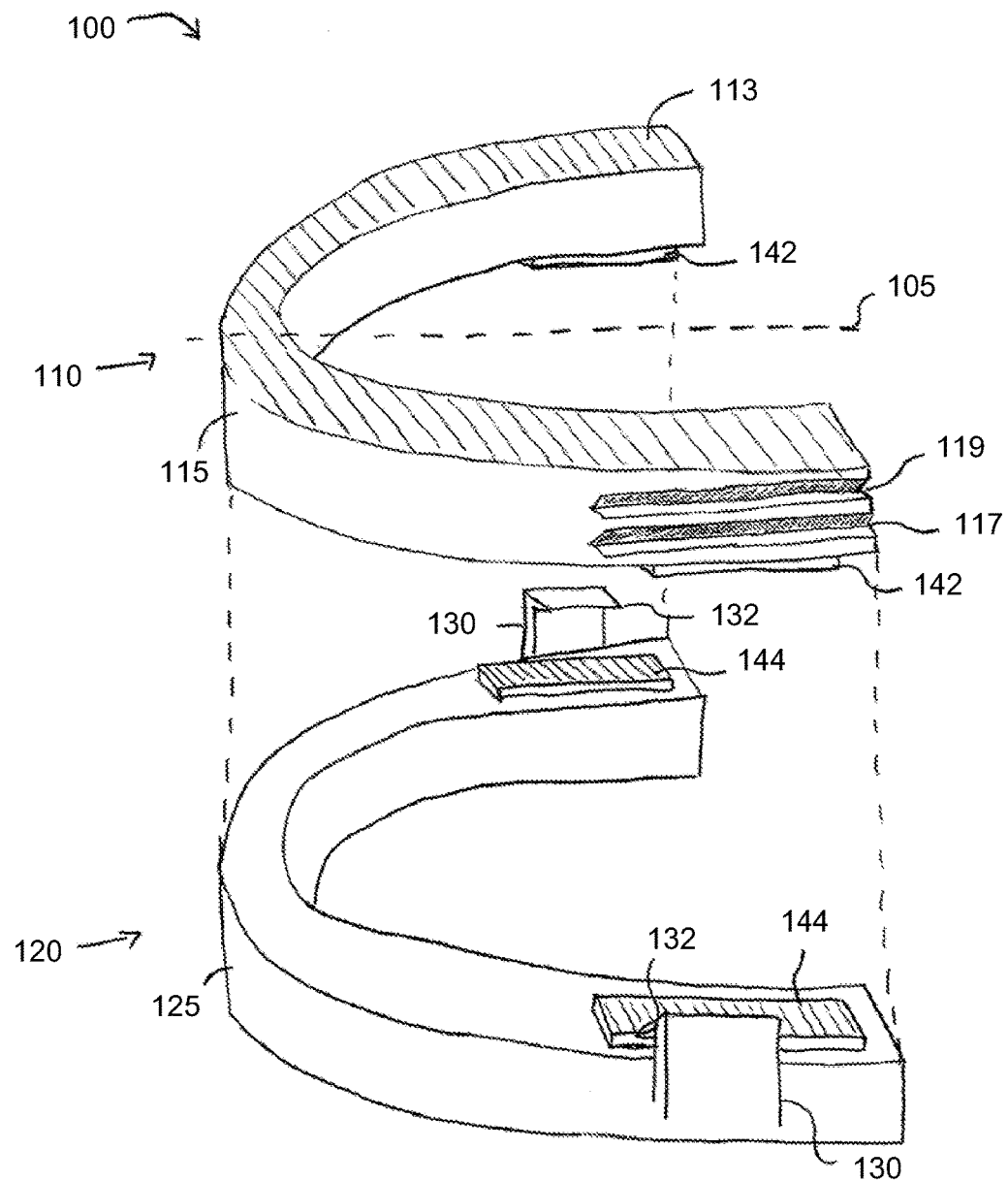
FIG. 1 illustrates a perspective view of an exemplary mandibular repositioning device with longitudinal flexibility in accordance with embodiments of the present technology.

The present technology provides a mandibular repositioning device (MRD) which may be self-titratable and self-fitting. The mandible may be repositioned relative to the maxilla, e.g., the mandible may be brought, via the device, to a position forward of a neutral resting and/or bite position. The MRD may maintain the user mandible in a single forward position or be re-adjusted to an alternate forward position for the mandible. The MRD may also allow movement of the mandible in a lateral direction. The lateral movement may be allowed while maintaining the forward position of mandible. The MRD of the present technology may provide for re-adjustable forward longitudinal positioning of the mandible and lateral movement while maintaining the forward positioning of the mandible using a plurality of components that are coupled together and allow for directional motion between each other.

Repositioning of the mandible in a forward position may have several benefits. If the device is used while the user is sleeping, the forward position of the mandible may open the user's airway and reduce vibration of the soft palate against the uvula, thereby reducing snoring. A mandibular repositioning device may be used to treat obstructive sleep apnea in a similar manner.

An MRD of the present technology may be adjusted in several ways. The MRD may adjust in a longitudinal direction to position a user's mandible in a desired forward position. The MRD may include a lockable mechanism for securing a position of the mandible. The lockable mechanism may be unlocked and then relocked to allow a user to further adjust the longitudinal position. The MRD may also allow lateral movement of the lower component of the MRD, relative to the upper component, thereby allowing the mandible to move from side to side. The mechanism which facilitates this lateral movement may allow for the mandible to travel in a straight line from side to side or along an arc, curve or other non-linear path. Allowing this lateral movement may be beneficial to people who grind their teeth at night, a dental condition called bruxism.

An MRD of the present technology provides several advantages. For instance, it allows the user to more easily adjust the degree of mandibular advancement. This adjustment, or titration, may be conducted any number of times, i.e. the user is not limited to the particular setting of advancement as selected in the initial fitting process. In addition, since the device, in preferred embodiments, is manufactured from plastic, production costs may be relatively low and the user may experience enhanced comfort while using the device.

The MRD of the present technology is easier to titrate than previous MRDs. For example, a user may advance his or her jaw as much as is comfortable and may then "lock" it in place. Previous MRD designs do not allow this type of "user-titratable" process. The present technology also allows the user to fit it to his or her mouth in a way that is based on comfort and also allows users to repeat the process as needed to strike the best balance between comfort and efficacy. Hence, the MRD of the present technology is oriented towards empowering the user to titrate the device without the assistance of a dentist or other health professional.

The present technology allows fabrication of an MRD entirely from low-cost injection molded plastics that may be easily titrated as many times as desired. Previous MRD devices must either use hardware that is more expensive, utilize elastic bands that wear-out and stretch, and they are only available in discreet sizes, thereby limiting the degree of advancement to specific discreet levels.

In previous self-molded or "boil-and-bite" devices, one would normally fit the upper and lower components to the mouth at the same time to insure that they are properly aligned laterally. However since one version of the present technology allows lateral movement, the upper component may be fitted to the upper teeth, and then separately, the lower component may be fitted to the lower teeth. This process of individually fitting the components of the MRD provides substantial advantages, including the possibility of making the self-fitting process easier for the user.

FIG. 1 illustrates a perspective view of an exemplary mandibular repositioning device with longitudinal flexibility in accordance with embodiments of the present technology. The device 100 includes an upper component 110 and a lower component 120 which are substantially symmetric with respect to a longitudinal axis 105 as shown. The upper component 110 may include a tray region 113 and a face 115.

The face 115 may include two substantially parallel grooves, a loose groove 117 and a tight groove 119, as shown. The lower component 120 may include a face 125 and a clip 130. The clip 130 may include a tip 132, which may couple with the loose groove 117 and/or the tight groove 119. The upper component 110 as shown in FIG. 1 may receive upper teeth of a user via the tray region 113. Similarly, the lower component 120 may receive lower teeth of the user (lower component tray region not shown in FIG. 1). The upper component 110 and the lower component 120 may include upper component friction pads 142 and lower component friction pads 144, as shown in FIG. 1.

Any number of elements 110-144 may be present in the design. For instance, though the exemplary embodiment of FIG. 1 illustrates a total of four friction pads 142 and 144 on the upper component 110 and the lower component 120, any number of friction pads 142 and 144 may be used. Friction pads 142 and 144 may be placed on either of the upper component 110, the lower component 120, or any combination thereof. Likewise, any number of clips 130 may be present in the device 100. As mentioned above, the device 100 may be substantially symmetric with respect to the longitudinal axis 105, therefore the face 115 may include an additional loose groove 117 and a tight groove 119.

The device 100 may be used as follows. The upper component 110 and the lower component 120 may be coupled to one another using the clip 130 and grooves 119 or 117. This may be accomplished by positioning the clip 130 within one of grooves 119 or 117 such that tip 132 slideably couples with the particular groove. In some embodiments, the clip tip 132 may first by coupled with the loose groove 117. The upper component 110 and the lower component 120 may be roughly aligned in a neutral resting and/or bite position setting as indicated by dashed lines while the clip tip is coupled with the loose groove 117. The coupled device 100 may be placed in this neutral setting into the mouth of a user.

In some embodiments, the tray region 113 may be further fitted and/or molded to the user's upper and/or lower teeth. The tray region 113 may be filled with a polymer and/or plastic. The device 100 may be heated, e.g. boiled in water, to soften the polymer and/or plastic. After heating, the user may bite down on the coupled device 100, leaving an impression of the user's teeth in the softened plastic. Alternatively, the upper component 110 and the lower component 120 may be separately heated and molded to the user's upper and lower teeth, respectively. The upper component 110 and lower component 120 may then be coupled by the clips 130 and the loose groove 117. The user's upper teeth may thus be secured in the tray region 113 of the upper component 110 and the lower teeth may be secured in the corresponding tray of the lower component 120. The user may, therefore, mold the device 100 to the upper and lower teeth.

Upon molding the device to the teeth, the user may then adjust, or titrate, a position of the lower component using the user's mandible. Movement of the mandible relative to the maxilla may move the lower component 120 relative to the upper component, changing the setting of the device 100 from a neutral position setting to an advanced position setting. As the user advances the mandible (e.g., extends the mandible outward), the clip 130 may slide along the loose groove 117. The clip 130 may slide along the loose groove 117 for any arbitrary distance that the user advances the mandible. The loose groove 117 and the tight groove 119 may therefore be of any arbitrary length along the face 115 in order to accommodate various distances of advancement.

The user may manipulate the device to select a position of advancement for the mandible with respect to the maxilla. The user may select the position due to, for instance, the user's comfort at the position of advancement. The user may then apply pressure to the device 100, e.g., by biting down on the upper component 110 and the lower component 120. The application of pressure may uncouple the clip 130 from the loose groove 117 and cause the clip 130 to couple with the tight groove 119. This adjustment of the coupling between the components (e.g., clip 130 engaged with tight groove 119 rather than with loose groove 117) brings the upper component and lower component closer together. Upon coupling adjustment with the tight groove 119, the clip 130, and therefore, the lower component 120, is no longer able to freely slide relative to the upper component 110.

In some embodiments, the upper component and lower component are not able to slide when clip is coupled with the tight groove due to the friction pads 142 and 144. The coupling of the clip 130 with the tight groove 119 may bring the friction pads 142 and 144 on the upper component 110 and the lower component 120 in contact with one another. The friction pads 142 and 144 may include, for instance, pads of finely-spaced grooves on, for instance, the upper component 110, that would mate with similar pads of finely-spaced grooves on the lower component 120. The friction pads 142 and 144 may be of any size and any placement on the upper component 110 and lower component 120, despite the configuration of the exemplary embodiment illustrated in FIG. 1. When in contact with each other (e.g., when the upper component and lower component are coupled via the clip and the tight groove 119), the friction pads 142 and 144 on the upper component 110 and the lower component 120, may prevent sliding of the lower component 120 relative to the upper component 110.

Figure 2:
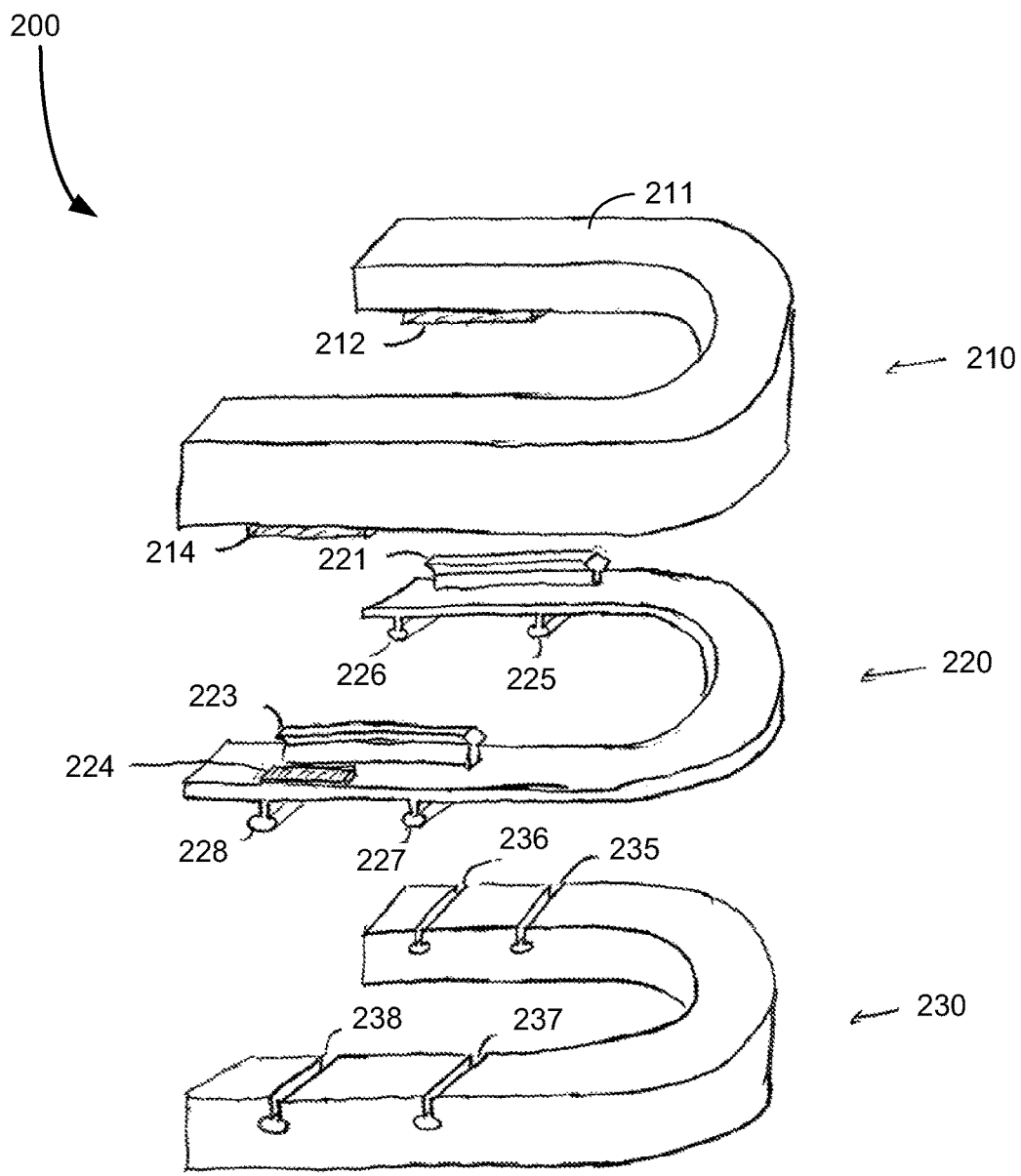
FIG. 2 illustrates a perspective view of an exemplary mandibular repositioning device with longitudinal and lateral flexibility in accordance with embodiments of the present technology.

FIG. 2 illustrates a perspective view of an exemplary mandibular repositioning device (MRD) 200 with longitudinal and lateral flexibility in accordance with embodiments of the present technology. The MRD of FIG. 2 has an upper component 210, intermediate component 220, and lower component 230, all of which may be substantially symmetric to a sagittal axis, which with respect to the human body, is the plane that would divide the body into the right and left half. Hence, the device may be plane-symmetric.

The upper component 210 and lower component 230 engage a user's teeth similar to the MRD of FIG. 1. In particular, the upper component 210 may include a tray 211 that receives the user's upper teeth, similar to tray region 113 of the MRD of FIG. 1. Lower component 230 may include a tray that receives the user's lower teeth. The intermediate component 220 may be used to engage the upper component and lower component and provide for longitudinal and lateral movement direction.

Upper component 210 may engage with the upper half of intermediate component 220 to provide adjustable positioning in the longitudinal direction. Upper component 210 may include friction pads 212 and 214 on a lower surface of the component. Friction pads 212 and 214 may make contact with friction pads 222 and 224 (see FIG. 3) on intermediate component 220 to help reduce, limit, or prevent movement in the longitudinal direction when the upper component 210 and intermediate component 220 are engaged in a tight fit (as opposed to a loose fit).

Figure 5:
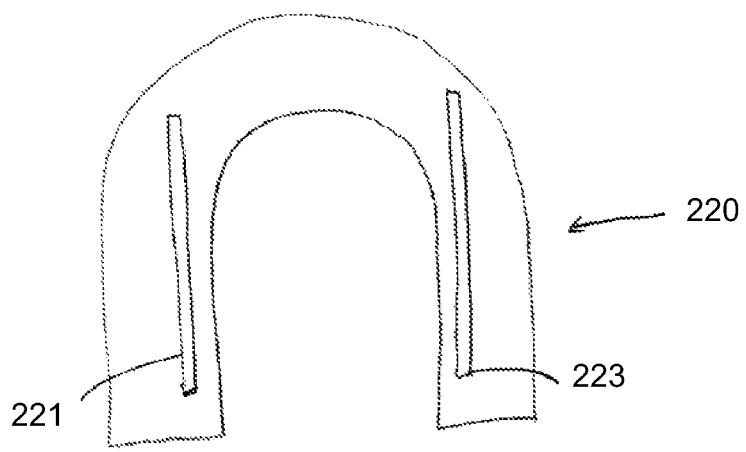
FIG. 5 illustrates a top view of an upper component of an exemplary mandibular repositioning device in accordance with embodiments of the present technology.

Intermediate component 220 includes upper rails 221 and 223 that extend along each end of the intermediate component in the longitudinal direction. The upper rails 221 and 223 may be substantially parallel along the longitudinal direction, as illustrated in FIG. 5. The upper rails may engage grooves of upper component 210 as discussed below.

Figure 3:
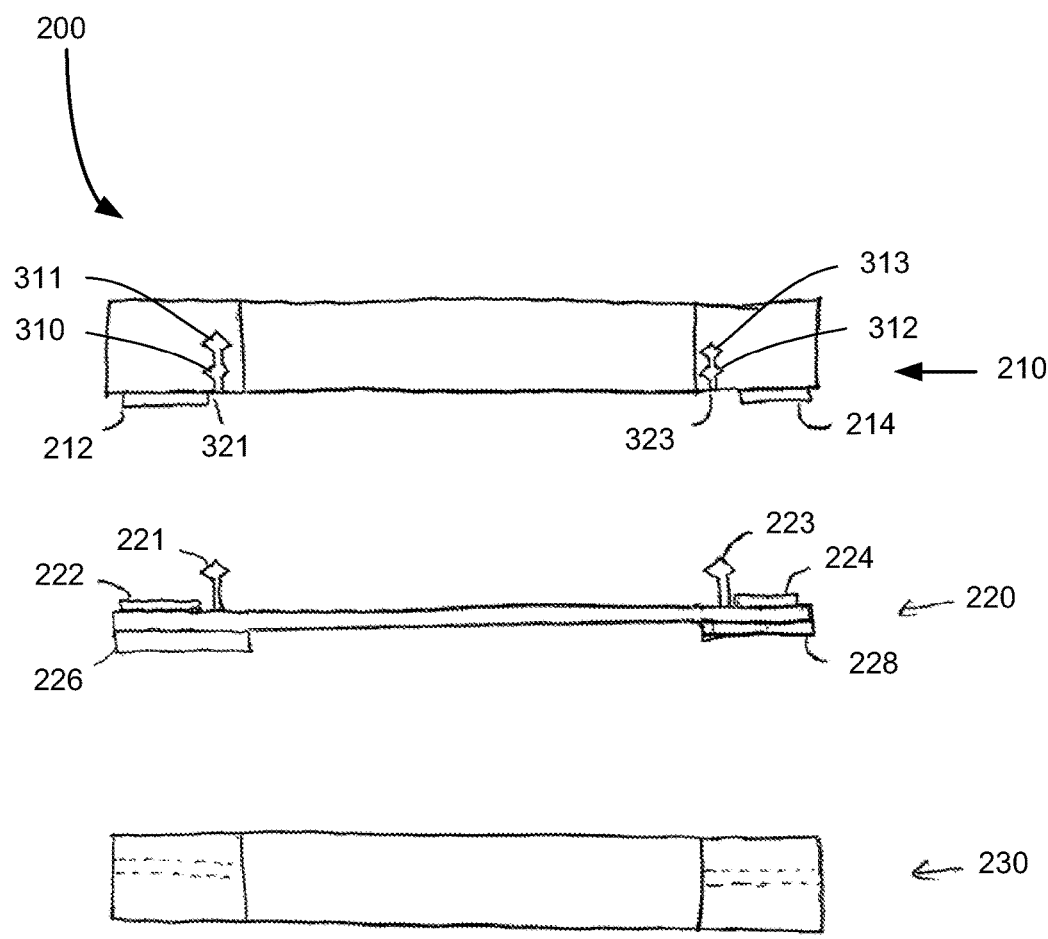
FIG. 3 illustrates an end view of an exemplary mandibular repositioning device with longitudinal and lateral flexibility in accordance with embodiments of the present technology.

FIG. 3 illustrates an end view of the exemplary MRD 200 with longitudinal and lateral flexibility in accordance with embodiments of the present technology. As illustrated in FIG. 3, upper component 210 includes grooves 321 and 323 that begin at each end of upper component 210 and extend into the component. Grooves 321 and 323 each have two portions with a wider aperture, corresponding to a loose position and a tight position. In particular, groove 321 has a loose position 310 and tight position 311 and groove 323 has a loose position 312 and tight position 313. Upper rails 221 and 223 of intermediate component 220 may engage groove loose positions 310 and 312, respectively, for a loose fit, during which the upper component and lower component may travel in a longitudinal direction. Upper rails 221 and 223 of intermediate component 220 may engage groove tight positions 311 and 313, respectively, to achieve a tight fit between the upper component and the intermediate component. When the upper rails and grooves are positioned in a tight fit, friction pads 212 and 214 of upper component 210 may engage (i.e., may come in contact with) friction pads 222 and 224 of intermediate component 220, thus preventing the upper component 210 and intermediate component 220 from moving in a longitudinal direction.

Intermediate component 220 may also have a lower set of rails which engage with grooves in lower component 230 to provide for lateral movement in the MRD. As illustrated in FIG. 2, lower rails 225, 226, 227 and 228 on a lower surface of intermediate component 220 may engage grooves 235, 236, 237 and 238 on an upper surface of the lower component. The lower rails may engage the grooves on the lower component to allow lateral movement between the intermediate component and the lower component. The mechanism formed by the lower rails and lower component grooves enables the MRD to allow a user to adjust their mandibular from side to side while the MRD is positioned in place within the user's mouth.

Figure 6:
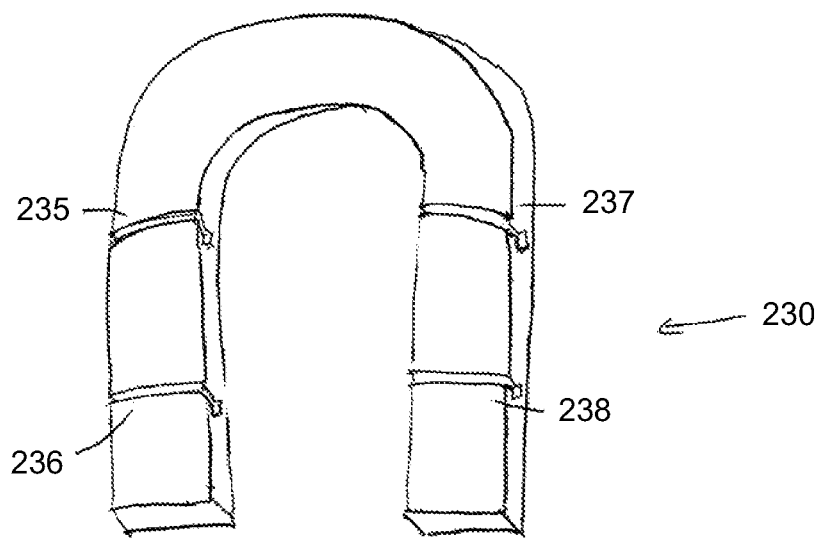
FIG. 6 illustrates a top view of a lower component of an exemplary mandibular repositioning device in accordance with embodiments of the present technology.

The lower rails of intermediate component 220 and the grooves of lower component 230 may have variety of configurations. For example, the lower rails and grooves may be shaped to allow movement in a curved lateral direction rather than a straight line of lateral direction. FIG. 6 illustrates a top view of an exemplary MRD lower component. The lower component 230 of FIG. 6 includes grooves which are curved or arced. The grooves 235, 236, 237 and 238 may be curved around to allow for a more natural range of motion for a mandible. For example, the outer portion of mandible (the portion near the front of the teeth) may travel in a lateral direction along a bit of a curve since the opposite end of the mandible is secured to the user's skull. Hence, the grooves and the lower rails may be shaped along a somewhat curved lateral trajectory to allow a more natural range of mandible movement.

The lower rails in the intermediate component that engage with the grooves in the lower component may have different formations. In addition to a shape that extends for a substantial part of the component end width, the rails may have the form of a tab that extends for smaller portion of the width, such as 50%, 40%, 30%, 20%, or some other portion of the component end width. The tab provides less surface area (compared to a rail which extends for most or all of the component end width) for the engagement between the lower component and the intermediate component, and therefore creates less friction between the two components as a tab travels along a groove. With less friction during movement, the MRD may provide for easier lateral movement for a mandible fitted with the MRD. Hence, tabs having a shorter length than the rails illustrated in FIGS. 2-3 may be used in place of rails discussed herein.

The lower rails and the grooves of the intermediate component may also be constructed with materials that provide for less friction. For example, the lower rails, grooves, or both may be coated or constructed with Teflon or some other material with low surface friction and suitable to be used as part of an MRD device.

The longitudinal mechanism may also include features for providing for less friction. For example, the upper rails 221 and 223 may be implemented as tabs that extend a shorter length than that of a rail. For example, FIG. 4 discloses an MRD 400 having a longitudinal mechanism having tabs that are shorter than rails 221 and 223. Additionally, longitudinal mechanism upper rails 221 and 223, and/or grooves that engage the rails, may be coated or constructed with Teflon or some other material with low surface friction and suitable to be used as part of an MRD device. An MRD may include a single tab to engage a groove or multiple tabs to engage one or more grooves of the MRD.

Figure 4:
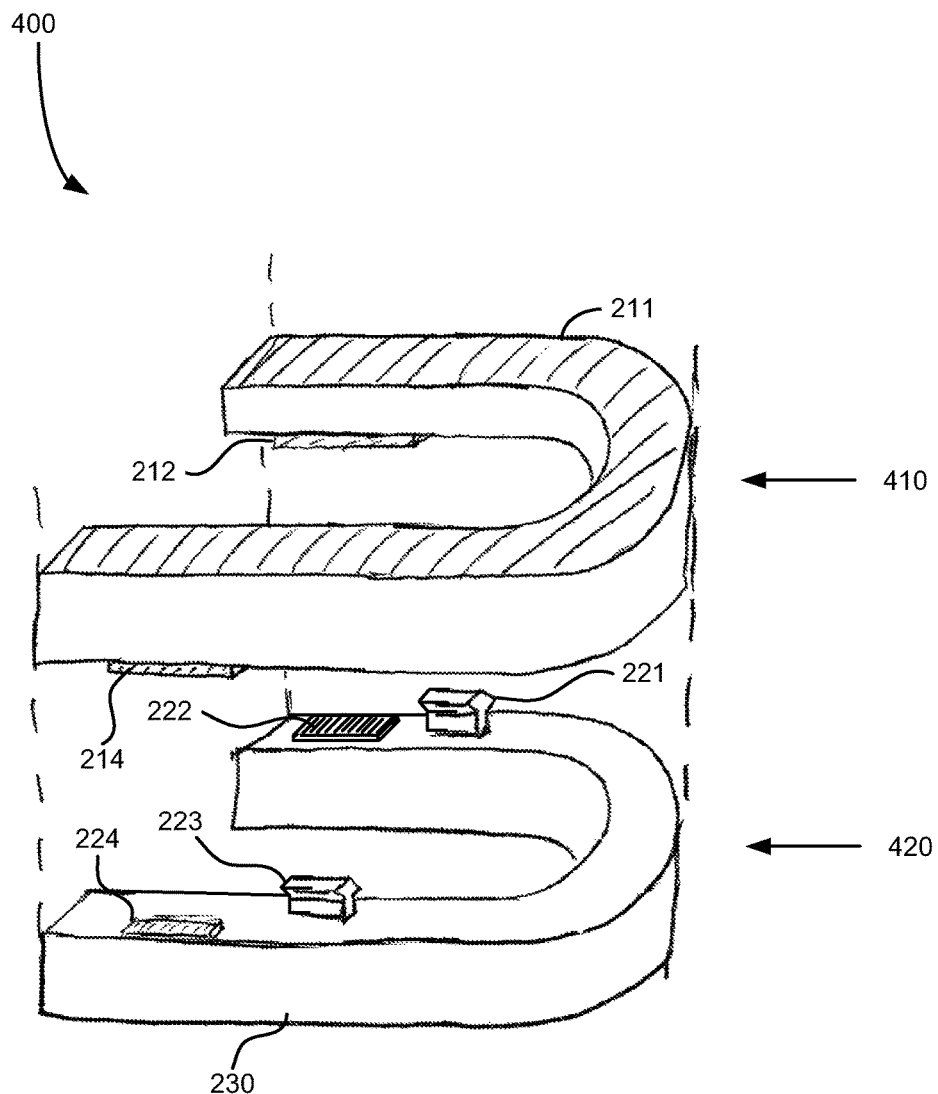
FIG. 4 illustrates a perspective view of an exemplary mandibular repositioning device with longitudinal flexibility in accordance with embodiments of the present technology.

The embodiments illustrated in FIGS. 1-3 are exemplary, and variations and combinations are within the scope of the present technology. For example, FIG. 4 illustrates a perspective view of an exemplary MRD 400 with longitudinal flexibility in accordance with embodiments of the present technology. The MRD 400 includes upper component 410 and lower component 420. Upper component 410 includes friction pads 212 and 214 and grooves on each end (similar to the tabs pictured in the upper component 210 of FIGS. 2-3). Lower component 420 includes tabs 221 and 223 and a friction pad on each end (pad 224 and pad 222).

Similar to MRD 100 in FIG. 1, the upper component 410 of MRD 400 may be positionally adjusted and "locked-in" to position along a longitudinal axis with respect to lower component 230. However, the upper component 410 and lower component 420 of MRD 400 utilize the longitudinal adjustment mechanism discussed with respect to MRD 200 of FIG. 2. Hence, MRD 400 may incorporate longitudinal adjustment using tabs 221 and 223 on the top surface of one component which engage grooves in the other component. Tabs 221 and 223 may be on a top surface of lower component 420 and the grooves may be incorporated into the bottom surface of upper component 410 (or vice versa). Similar to MRD 200, friction pads 212 and 214 on upper component 410 may make contact with friction pads 222 and 224 (see FIG. 3) on intermediate component 220 to help reduce, limit, or prevent movement in the longitudinal direction when the upper component 210 and intermediate component 220 are engaged in a tight fit (as opposed to a loose fit).

One or more components in an MRD of the present technology may be constructed from different types of materials. Portions of components of the MRD of FIGS. 2-3 may be constructed from an acrylic polymer, titanium, or some other material suitable for use within a user's mouth. For example, the intermediate component may be built mostly from an acrylic polymer but may have titanium rails to provide for extra strength. Other materials may also be used in construction of an MRD of the present technology.

The means of engagement between MRD components may vary from that discussed with respect to the exemplary embodiments above. For example, the exemplary MRD illustrated in FIGS. 2-3 shows intermediate component 220 with rails that engage grooves formed in the upper and lower components. An MRD with an upper, intermediate and lower component may include rails on a lower surface of the upper component that engage "upper" grooves in the intermediate component, rails on an upper surface of the lower component that engage "lower" grooves in the intermediate component, or both. Similarly, the lateral mechanism may be implemented in the upper and intermediate components and the longitudinal component may be provided in the lower and intermediate components.

An MRD of the present technology may also include a combination of features from the MRDs illustrated in FIGS. 1-3. For example, an MRD may only have two components and only provide longitudinal movement using a mechanism as illustrated in FIGS. 2-3 (rails and grove in longitudinal direction), only two components and only provide lateral movement using a mechanism as illustrated in FIGS. 2-3 (rails and grove in lateral direction), and three components with longitudinal movement provide by grooves and clips similar to the exemplary MRD of FIG. 1 and the lateral movement mechanism of FIGS. 2-3.

The configuration and number of elements of the MRD of FIGS. 2-3 are exemplary and are not intended to limit the scope of the present technology. For example, though only two upper rails are illustrated in the intermediate component 220, additional or fewer rails may be implemented along with corresponding grooves. Similarly, additional or fewer friction pads, having the same or different size and shape, may be implemented in the MRD of FIGS. 2-3.

In operation, MRD 200 may be used by coupling upper component 110 and the intermediate component 120 together using rails 221 and 223 with grooves 321 and 323. This may be accomplished by positioning the rail 221 within groove position 310 or 311 and rail 223 within groove position 312 or 313, such that each rail slideably couples with the particular groove.

In some embodiments, rails 221 and 223 may be coupled with the loose position grooves 310 and 312, respectively. The upper component 210 and the intermediate component 220 may be roughly aligned in a neutral resting and/or bite position setting within the mouth of the user such that the front of each component are vertically aligned.

Tray region 211 may be fitted and/or molded to the user's upper teeth. A corresponding lower tray region in a lower component may be fitted to the user's lower teeth. The fitting of tray region 211 (and a corresponding lower tray in lower component 230, if applicable) may be performed similarly to tray region 113 of MRD 100. The user's upper teeth may thus be secured in tray 211 of the upper component 210 and the lower teeth may be secured in a corresponding tray of the lower component 230. The user may, therefore, mold the device 200 to the upper and lower teeth.

With most MRDs, the upper and lower components would be fit at the same time to insure that the upper and lower components are laterally aligned properly. However, in the present technology that allows lateral movement, there would be no need to insure proper lateral alignment because the device allows movement in this axis. Therefore, when using an MRD of the present technology, it may be possible to fit the upper component to the upper teeth, and separately, fit the lower component to the lower teeth. Such an approach may provide other benefits.

Upon molding the device to the teeth, the user may then adjust, or titrate, a longitudinal position of the lower and intermediate component using the user's mandible. Movement of the mandible relative to the maxilla may move the intermediate component and lower component relative to the upper component, changing the setting of the device 100 from a neutral position setting to an advanced position setting. As the user advances the mandible, the rails 221 and 223 may slide within loose groove positions 310 and 312. The loose groove 117 and the tight groove 119 may be of any arbitrary length along the length of the MRD in order to accommodate various distances of advancement.

The user may manipulate the device to select a position of advancement for the mandible with respect to the maxilla. The user may select the position due to, for instance, the user's comfort at the position of advancement. The user may then apply pressure to the device 200, e.g., by biting down on the upper component 210 and the lower component 230. The application of pressure may uncouple rails 221 and 223 from the loose groove positions 310 and 312 and cause the rails to couple with the tight groove positions 311 and 313. This adjustment of the coupling between the components (e.g., upper rails engaged with tight position grooves 311 and 313 rather than with loose position grooves 310 and 312) brings the upper component closer to the intermediate component. Upon coupling adjustment with the tight position grooves 311 and 313, the rails 221 and 223, and therefore, the intermediate component 220, are no longer able to freely slide in a longitudinal direction relative to the upper component 110. Similar to the MRD 100 of FIG. 1, the upper component 210 and intermediate component 220 are not able to slide when a rail is coupled with tight position grooves 311 and 313 due to friction between upper component friction pads 212 and 214 and intermediate friction pads 222 and 224.

As mentioned above, the lower component 230 and intermediate component 220 include rails and grooves that may engage each other to provide movement in a latitudinal direction. Once the MRD is molded to a user's teeth and positioned within the user's mouth, the MRD 200 may allow the user to move the mandible from side to side. As a user moves the mandible from side to side in a latitudinal direction, the lower component moves in the direction of grooves coupled to the lower rails of the intermediate component. By allowing the grooves to move along the rails, the lower component may move from side to side as the user moves their mandible, for example when a user would normally be grinding their teeth.

It is intended that the MRD devices discussed herein are to be used with and fitted to a mandible of a user. Hence, the actual size and shape of the MRD components and portions thereof may differ from the shapes and sizes illustrated in FIGS. 1-5. The drawings of the MRDs are provided for purposes of discussion and general illustration, and may not be to scale of an actual MRD of the present technology.

Upon reading this disclosure, it will become apparent to one skilled in the art that various modifications may be made to the mandibular repositioning device disclosed without departing from the scope of the disclosure. As such, this disclosure is not to be interpreted in a limiting sense. For instance, the mandibular repositioning device may be manufactured out of plastic, metal, a polymer, a combination of these elements, or other materials. As such, the device may be fit to the user's upper and lower teeth via a boil-and-bite fitting process. However the present technology may also be applied to custom-fabricated MRDs which are typically constructed in a dental lab from a plaster casting of the user's teeth such that the resulting device may then fitted to the patient's mouth by a dentist or by the user without the assistance of a dentist.

What is claimed is:

1. A mandibular re-positioning device, comprising:
   a first component adapted to receive a user's top teeth and a second component adapted to receive the user's bottom teeth and an intermediate component adapted to fit between the upper component and the lower component and to couple the upper and lower components;
   a first mechanism coupling together the upper component with the intermediate component;
   the first mechanism coupling the upper and intermediate components in either of two states comprising an unlocked state or a locked state;
   the unlocked state allowing the upper and intermediate components to slide, relative to each other, along a sagittal axis, thereby allowing the user's mandible to freely move in an anterior or posterior direction while the mandibular re-positioning device is positioned within the user's mouth;
   the locked state bringing the first component into closer contact with the intermediate component, thereby preventing the two components from sliding, relative to each other, along the sagittal axis, thereby preventing any change in mandibular advancement while the mandibular re-positioning device is positioned within the user's mouth;
   the first mechanism being able to transition from the unlocked state to the locked state through application of a force along a vertical axis, the force coming from the user biting down;
   a second mechanism coupling together the intermediate component with the second component and adapted to allow movement of the user's mandible in a lateral direction while the mandibular re-positioning device is positioned within the user's mouth; and
   the second mechanism including a groove along the lateral direction within the second component, the groove coupling to a rail or to a tab on the intermediate component that travels within the groove, the groove being curved within the second component to match a natural movement of the user's mandible.

2. The mandibular re-positioning device of claim 1, further comprising areas on the first component and on the intermediate component for direct contact with each other while in the locked state and which are designed to maximize friction, along the sagittal axis by incorporating rough texture or interlocking structures.

* * * * *

UNITED STATES PATENT AND TRADEMARK OFFICE
CERTIFICATE OF CORRECTION

PATENT NO. : 10,137,030 B2
APPLICATION NO. : 14/158850
DATED : November 27, 2018
INVENTOR(S) : Noel Lindsay et al.

Page 1 of 1

It is certified that error appears in the above-identified patent and that said Letters Patent is hereby corrected as shown below:

On the Title Page

Item (63), "now Pat. No. 9,631,800" should read -- now Pat. No. 8,631,800 --

Signed and Sealed this
Eighth Day of January, 2019

Andrei Iancu
*Director of the United States Patent and Trademark Office*